United States Patent [19]

Lorenz et al.

[11] 4,275,165

[45] Jun. 23, 1981

[54] PROCESS FOR ISOLATING HEPATITIS A-VIRUS

[75] Inventors: Peter R. Lorenz; Ernst Weinmann, both of Marburg; Mirko Majer, Fürth, all of Fed. Rep. of Germany

[73] Assignee: Hoechst Aktiengesellschaft, Frankfurt am Main, Fed. Rep. of Germany

[21] Appl. No.: 54,609

[22] Filed: Jul. 3, 1979

[30] Foreign Application Priority Data

Jul. 6, 1978 [DE] Fed. Rep. of Germany ....... 2829741

[51] Int. Cl.³ .............................................. C12N 7/00
[52] U.S. Cl. ................................................... 435/235
[58] Field of Search ....................................... 435/235

[56] References Cited

PUBLICATIONS

American Society of Microbiology, Annual Meeting-1976, S-249.
American Society of Microbiology, Annual Meeting, Abstracts, vol. 76, 1976, S-250.
Hersey et al, Laboratory Investigation, vol. 19, No. 5, pp. 558-568.
Feinstone et al, Journal of Virology, vol. 13, No. 6, pp. 1412-1414, Jun. 1974.
Provost et al, Proc. Soc. Exp. Biol. Med. 142; pp. 1257-1267 (1973).
Prince et al, Perspectives in Virology, vol. 7, Chap. 14, pp. 241-296, pp. 287-290 pert. (W3 PE58, V. 9 1971).

*Primary Examiner*—Ethel G. Love
*Attorney, Agent, or Firm*—Curtis, Morris & Safford

[57] ABSTRACT

What is disclosed is a method for obtaining hepatitis-A virus by infecting monkeys with the virus and then isolating the virus from the faeces of the monkeys.

7 Claims, No Drawings

PROCESS FOR ISOLATING HEPATITIS A-VIRUS

This invention relates to a process for isolating hepatitis A-virus, which is the carrier of the specific hepatitis A-antigen.

At present, the pathogen causing viral inflammation of the liver, i.e. the hepatitis A-virus, is isolated from the faeces of affected persons. This method is disadvantageous in that a large number of patients is required for isolating the raw material, which is only available, for example, on the appearance of an epidemic of hepatitis A.

The hepatitis A-virus is also isolated from the liver of marmosets and anthropoids of the species Sanguinus (S.) mystax, S.nigricollis, S.fuscicollis, S.oedipus, Callithrix (C.)jacchus, C.argentata, Cercopithecus aethiops, Pantroglodytes and Anthropopithecus troglodytes. All the aforesaid species are, however, menaced with extinction and, in general, they can only be bred with considerable expenditure and little success. To isolate the hepatitis A-virus from the liver, the donor animals must be sacrified.

According to the present state of scientific knowledge, the hepatitis A-virus cannot be cultivated in tissue cultures.

The present invention provides a process for isolating hepatitis A-virus, which comprises infecting monkeys, especially of the family of Callithrididae, preferably *Callithrix jacchus,* with hepatitis A-virus and isolating the hepatitis virus from the faeces of the monkeys.

It is a further feature of the process of the invention to treat the animals with immune suppressors.

It proved advantageous to administer to the animals an immune suppressor over a period lasting from a few days, preferably three days, prior to infection with hepatitis A-virus to approximately nine days after infection. Suitable immune suppressors in the sense of the invention are those suppressing the humoral immunity as well as those suppressing the cellular immunity. From among the first group, cortisone is mentioned by way of example, while the second group includes, for example, cyclophosphamide. It is likewise possible to use other immune suppressors which do not belong to either one of the mentioned groups, for example antilymphocyte globulin, or any other measure to suppress the immune reaction, for example radiation.

Best results are obtained when an immune suppressor is administered daily and when immune suppressors with different ways of action are given by turns. According to a preferred embodiment, one day cortisone and the next day cyclophosphamide are alternately given to the infected monkeys. The immune suppressor is administered one time per day. If necessary, it can also be administered in greater intervals, for example every second day. The dose should be near the upper limit of tolerance, which is about 5 mg/kg with cortisone and about 10 mg/kg with cyclophosphamide.

The effect of the immune suppressors is controlled by counting the white blood cells. Normally, 1 cc of blood contains 4,000 to 7,500 white cells. The administration of an immune suppressor reduces the number of white blood cells to about 2,500. As soon as the number of the white corpuscles has dropped below 2,000, the immune suppression is discontinued.

The faeces of the animals are collected for about 30 days beginning with the day of infection and stored at $-20°$ C. The hepatitis A-virus is then isolated from the faeces. It is not necessary to kill the animals; after healing up of the infection, they can be used for breeding or for isolating hepatitis A-antibodies.

For the isolation of the hepatitis A-virus from the faeces of the monkeys, daily samples are immunologically examined as to the presence of hepatitis A-virus, for example by radioimmuno assay or immunoperoxidase test. To this end, small amounts of the faeces, about 100 mg, are suspended in 9 times the amount by weight of physiological sodium hydrochloride solution, the suspension is vigorosly shaken for 15 minutes in a mixing device and centrifuged to obtain a clear solution. In the supernatant, the hepatitis A-virus is determined.

The faeces portions found to be positive are suspended in about two to three times the amount by weight of physiological sodium chloride solution, thoroughly mixed and after some time (about 10 to 60 minutes) the liquid supernatant is separated from the solid matter. The resulting supernatant contains the hepatitis A-virus. If desired, it can be concentrated.

The amount of hepatitis A-virus obtained indicated that the faeces of a test animal infected with immune suppression yielded an amount of hepatitis A-virus sufficient for 5,000 tests. In an infection test without immune suppression the faeces contained a distinctly lower amount of hepatitis A-virus.

The isolated hepatitis A-virus is used as diagnostic agent for the detection of antibodies against hepatitis A-virus in patients suffering from liver inflammations. It can also be used for the manufacture of a vaccine and for obtaining hepatitis A-antibodies against hepatitis A-virus. It can be used likewise for carrying out the process according to the invention.

The following example illustrates the invention.

EXAMPLE

Two monkeys of the species Callithrix jacchus were treated for 12 days with immune suppressors. On the first and all following odd days cortisone was administered and on the second and all following even days, including the 12th day, cyclophosphamide was administered. On the third day, the monkeys were infected by injecting in the femoral vein 1 ml of a suspension of hepatitis A-virus isolated from the stool of hepatitis patients. The infected faeces collected each day up to the 30th day after infection were frozen and preserved at $-20°$ C. In the daily portions the presence of hepatitis A-virus was ascertained, the positive faeces portions were collected (73.5 g) and suspended in twice the amount by weight of physiological sodium chloride solution. The suspension was then shaken for 15 minutes on a mixer and centrifuged to obtain a clear solution. The resulting supernatant was sufficient for about 10,000 tests for hepatitis A-antibodies.

What is claimed is:

1. A method for obtaining hepatitis A-virus which comprises administering an immune suppressor to a monkey for a few days, then innoculating the monkey with hepatitis A-virus, continuing to administer an immune suppressor to the monkey, and recovering the virus in an aqueous extract of the faeces of the monkey.

2. A method as in claim 1 wherein said immune suppressor is administered to said monkey daily for three days prior to innoculation and for about nine days after innoculation.

3. A method as in claim 2 wherein, each day, an immune suppressor having a different immune suppressing mechanism is administered.

4. A method as in claim 3 wherein, on alternate days, an immune suppressor suppressing humoral immunity and an immune suppressor suppressing cellular immunity are administered.

5. A method as in claim 4 wherein, on alternate days, cortisone and cyclophosphamide are administered.

6. A method as in claim 1 wherein said monkey is from the family of Callithicidae.

7. A method as in claim 6 wherein said monkey is of the species *Callithrix jacchus*.

* * * * *